United States Patent [19]

Chambers

[11] Patent Number: 5,048,678
[45] Date of Patent: Sep. 17, 1991

[54] SELF-CONTAINED SURGICAL SUTURE PACKAGE

[75] Inventor: Elizabeth A. Chambers, Danbury, Conn.

[73] Assignee: American Cyanamid Company, Stamford, Conn.

[21] Appl. No.: 340,340

[22] Filed: Apr. 19, 1989

[51] Int. Cl.⁵ .............................................. A61B 17/06
[52] U.S. Cl. .................................... 206/63.3; 206/438
[58] Field of Search ................ 206/63.3, 438; 229/71, 229/68 R, 75

[56] References Cited

U.S. PATENT DOCUMENTS

| | | | |
|---|---|---|---|
| 311,946 | 2/1885 | Bishop | 229/75 |
| 724,237 | 3/1903 | Armstrong | 229/71 |
| 725,866 | 4/1903 | Patterson | 229/75 |
| 1,962,921 | 6/1934 | Tullar | 229/71 |
| 3,162,307 | 12/1964 | Regan, Jr. | 206/63.3 |
| 3,206,018 | 9/1965 | Lewis et al. | 206/63.3 |
| 3,280,971 | 10/1966 | Regan, Jr. | 206/63.3 |
| 3,444,994 | 5/1969 | Kaepernik et al. | 206/63.3 |
| 4,063,638 | 12/1977 | Marwood | 206/63.3 |
| 4,069,912 | 1/1978 | Black et al. | 206/63.3 |
| 4,126,221 | 11/1978 | Cerwin | 206/63.3 |
| 4,700,833 | 10/1987 | Smith | 206/63.3 |
| 4,884,681 | 12/1989 | Roshdy et al. | 206/63.3 |

FOREIGN PATENT DOCUMENTS 0186490  10/1922  United Kingdom ................. 229/71

Primary Examiner—Paul T. Sewell
Assistant Examiner—Jacob K. Ackun, Jr.
Attorney, Agent, or Firm—Charles F. Costello, Jr.

[57] ABSTRACT

This invention relates to a direct dispensing and self-contained surgical suture package. The package can comprise a first part having a strippable envelope, and a second part self-contained therein.

2 Claims, 4 Drawing Sheets

SELF-CONTAINED SURGICAL SUTURE PACKAGE

BACKGROUND AND SUMMARY OF THE INVENTION

This invention relates to a direct dispensing and self-contained surgical suture package. The package can comprise a first part having a strippable envelope, and a second part self-contained therein.

A direct dispensing and self-contained surgical suture package has been invented. In one embodiment, the package comprises a back panel; at least one side flap foldably connected to the back panel; a label flap foldably connected to the back panel and adjacent to the at least one side flap; and means for self-containing the direct dispensing surgical suture package. In a specific embodiment, the package comprises two opposite side flaps. In another embodiment, the package has a strand flap foldably connected to the back panel and opposite the label flap. In still another embodiment, the package has at least one retention slip contained in the at least one side flap.

In a more specific embodiment, the package comprises a back panel; two opposite side flaps foldably connected to the back panel; a label flap foldably connected to the back panel and adjacent to the side flaps; and means for attaching the label flap to the flaps. In one embodiment, the package has a strand flap foldably connected to the back panel and opposite the label flap. In another embodiment, the package has at least one retention slit contained in at least one side flap.

Another direct dispensing and self-contained surgical suture package has been invented. In this embodiment, the package comprises a first and second part. The first part has a strippable envelope. Self-contained within the first part is the second part. The second part has a back panel; at least one side flap foldably connected to the pack panel; a label flap foldably connected to the back panel and adjacent to the at least one side flap; and a chevron flap foldably connected to the label flap and opposite the back panel. The at least one side flap is folded onto the back panel, the label flap is at least partially folded onto the side flap and the chevron flap is inserted between the side flap and back panel. In a specific embodiment, the package has two opposite side flaps. In another specific embodiment, the package has a strand flap foldably connected to the back panel and opposite the label flap. In a further embodiment, the package has at least one retention slit contained in the at least one side flap.

DESCRIPTION OF THE DRAWINGS

FIG. 1 is a front view of an unfolded suture label with six panels;

FIG. 2 is a front view of FIG. 1 showing the strand cover panel 1 folded onto back panel 2;

FIG. 3 is a front view of FIG. 2 showing the front panel 3 and tuck panel 6 folded onto the back panel 2;

FIG. 4 is a back view of FIG. 3 inverted one hundred and eighty degrees and showing the side panels 4 and 5 folded onto the strand cover panel 1;

FIG. 5 is a back view showing the front panel 3 and tuck panel 6 of FIG. 4 rotated three hundred and sixty degrees, and then folded onto the side panels 4 and 5;

FIG. 6 is a back view of FIG. 5 showing the panel 6 tucked between the side panels 4 and 5, and the strand cover flap 1.

DETAILED DESCRIPTION

The suture label is and remains, before, during, and after suture dispensing, a single piece. The needle of the suture is visible within the label for easy access and removal of the suture from the label. The exposed needle is grasped with the hand or with a needle holder and by pulling gently and evenly, the suture is dispensed.

Referring to FIGS. 1 and 4 to 6, the label is designed to protect the suture strand from being in contact with the needle, therefore preventing the suture strand from being damaged. The needle holding slit(s) 7 located in the side panel 4 can be used to hold either needled or non-needled sutures.

Figure 1:
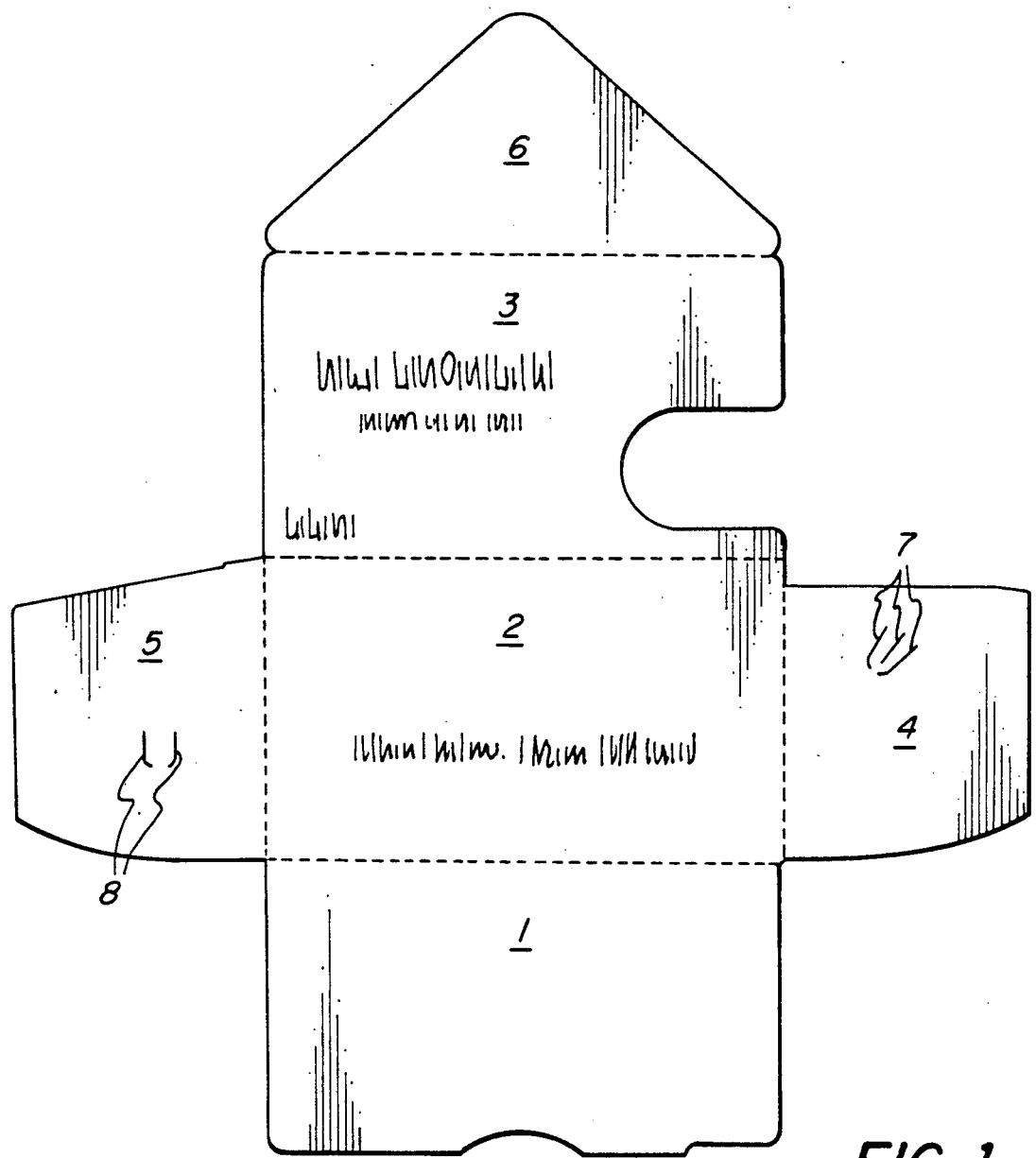
FIGS. 1 to 6 show the folding sequence of the suture package of this invention.
Figure 2:
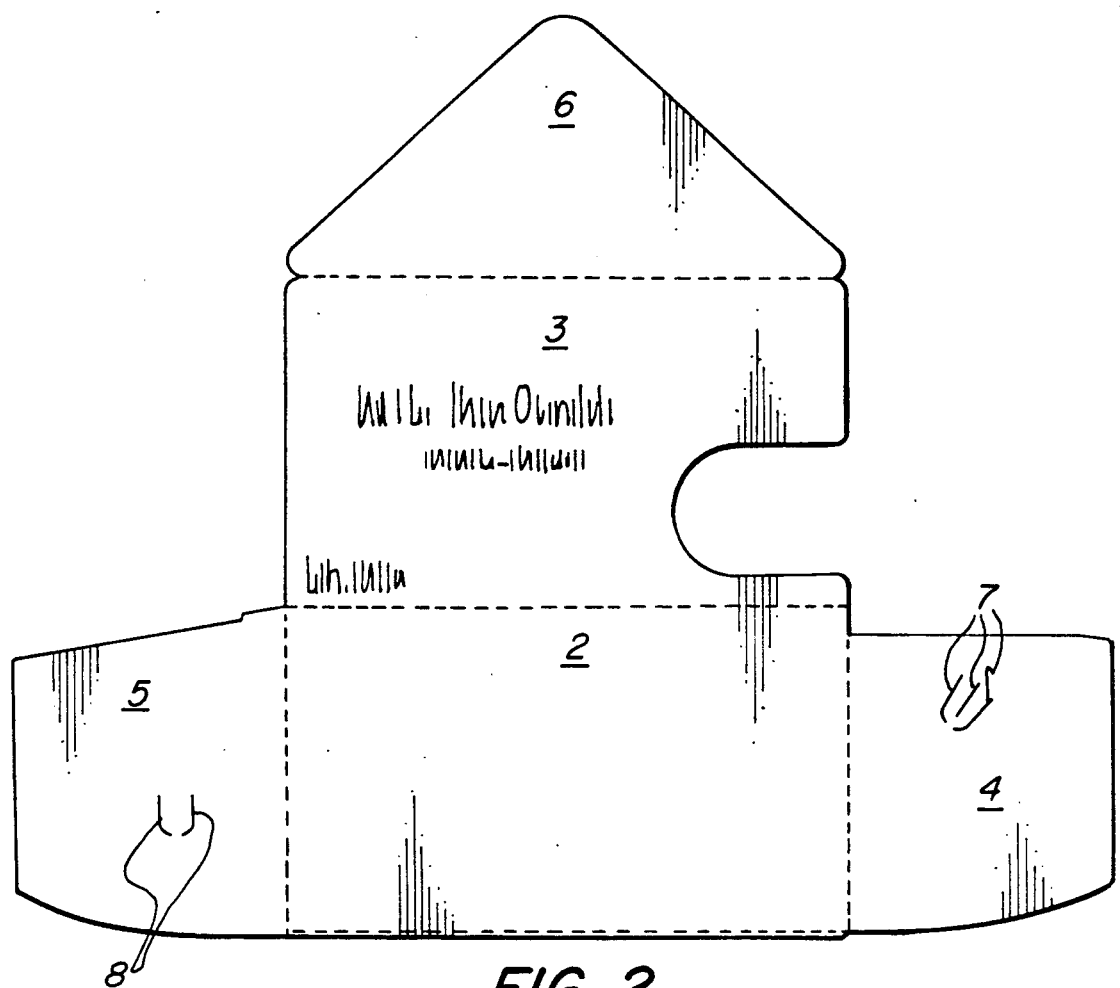
Figure 3:
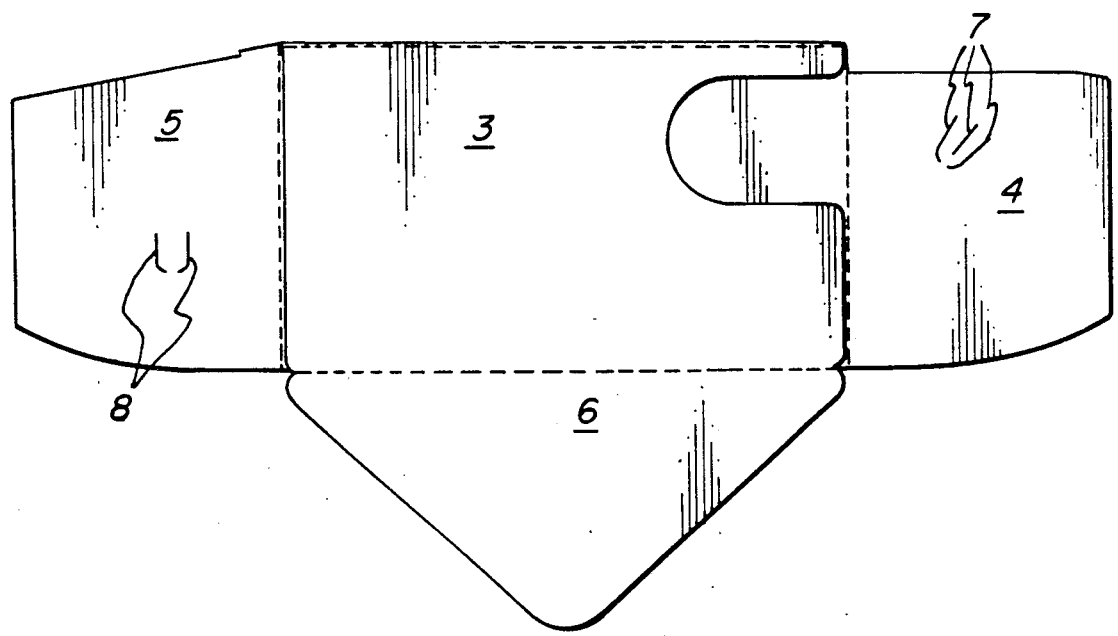

Referring to FIG. 1, the label is manufactured from sterilizable 90 pound offset paper capable of withstanding alcoholic solution, heat, steam, gas or radiation sterilization without adverse affects. The paper may be coated with about ½ mil polyethylene so as to make it heat sealable. Such paper is known in the trade, and is readily available. Sealing, if desired, can be accomplished by heat sealing dies, or by ultrasonic means.

Figure 6:
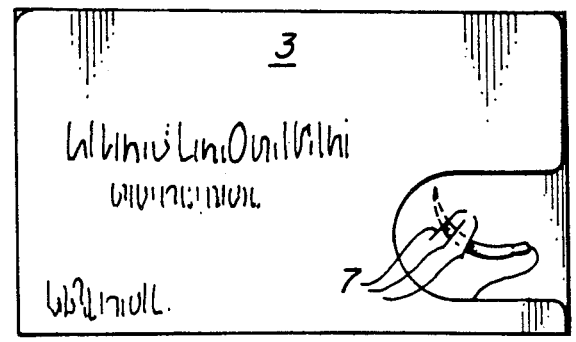

Referring to FIG. 6, the self-contained label can be placed into a strippable envelope. The envelope materials, the methods of manufacturing such materials, and the method of loading the label into the envelope are well known in the suture packaging art, e.g. as described in U.S. Pat. No. 4,069,912 FIG. 1 entitled "Suture Package", issued Jan. 24, 1978 to S. Black and D.C. MacRitchie, or U.S. Pat. No. 4,063,638 FIG. 1 entitled "Direct Dispensing Packaging of Surgical Sutures", issued Dec. 20, 1977 to R.K. Marwood. These patents are incorporated by reference. Referring to FIG. 1 of these patents, the strippable envelope 31 is peeled off. The peeling or stripping action is enhanced by the size and shape of the folded label in relation to the envelope 31.

Referring again to FIG. 6 of this invention, the suture label is self-contained. Also, after the suture is dispensed from the label, the label continues to be self-contained and in one piece. Therefore, only the surgical suture needle and/or strand(s), and the self-contained suture label are added to the operating area. Related hazards are thus minimized and accountability is simplified.

FIG. 1 shows a preferred suture label. The label is cut out and scored from a sheet of sterilizable paper which may be coated with polyethylene for heat sealing.

As shown in FIG. 1 to 4, the label consists of a back panel 2. Attached to the back panel is a strand cover panel 1, label cover or front panel 3, tuck panel 6, and side flaps 4 and 5. A retention slit or slits 7 located on the side panel 4 can anchor a needle of an appropriate size and shape in the desired orientation and position between the strand cover flap 1 and the side flaps 4 and 5. For a straight needle of sufficient length, another retention slit or slits 8 located on the other side panel 5 can be used to anchor the pointed end. For a curved needle, the desired orientation is usually such that the arc of travel from the barrel to the point is in a counter clockwise direction. The barrel of the needle protrudes through the retention slit on the panel 4, which is exposed through the round cutout in the panel 3 (shown in FIG. 6) for direct dispensing by hand or by needle holders. Alternatively, the retention slit or slits 7 can be used for a non-needled suture (or sutures).

Figure 4:
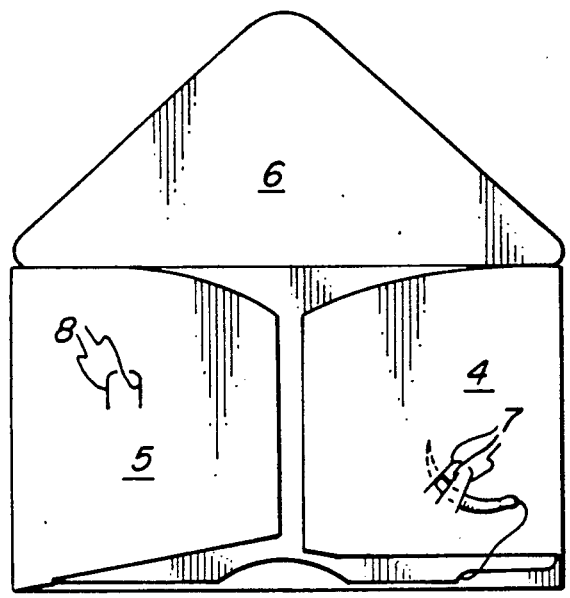

Referring to FIG. 4, the side panels 4 and are folded onto strand cover panel 1 for the purpose of loading the suture strand (or strands) into the label. In this configuration, the suture strand(s) are loaded into the label between the strand cover panel 1 and back panel 2. The configuration of the strand(s) in the label can be any series of loops or coils that allow the strand(s) to dispense freely from the label without tangling. A preferred strand configuration is that termed a FIG. eight. The loading of a suture strand into a label using the figure eight configuration is known in the prior art.

Figure 5:
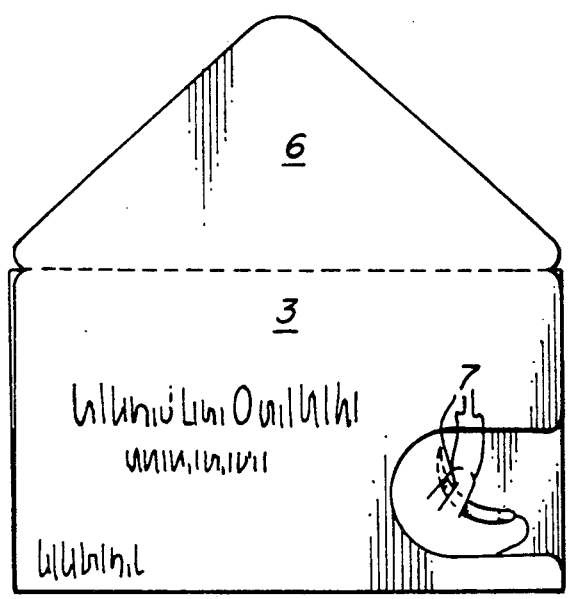

Referring to FIGS. 4 and 5, the front panel 3 is rotated and then folded onto the side panels 4 and 5. Referring to FIG. 6, the tuck panel 6 is tucked between the side panels 4 and 5, and the strand cover flap 1. In this configuration, the suture package is and remains self-contained and as one piece before, during and after dispensing of the suture.

FIG. 6 shows the label completely assembled, with the tuck panel 6 inserted (tucked) between the side panels 4 and 5, and the strand cover panel 1.

Figure 7:
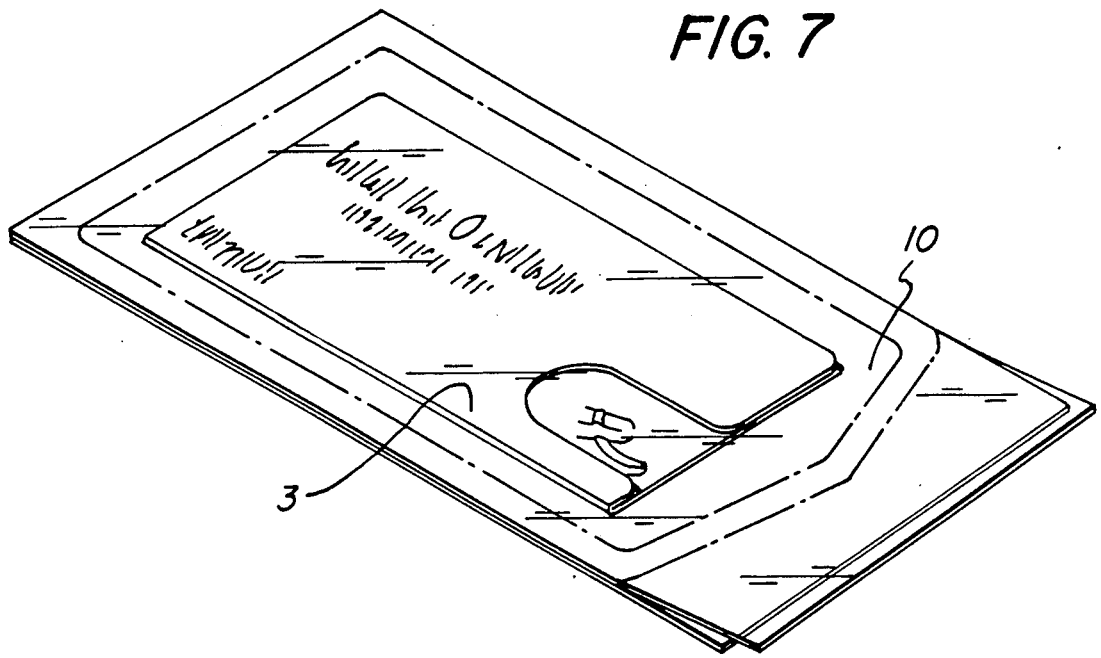
FIG. 7 is a perspective view showing the preferred loading of the suture package of FIG. 6 into a strippable envelope.

FIG. 7 describes the loading of the self-contained, one piece suture package of FIG. 6 into a strippable envelope 10. The loading of the suture package shown in FIG. 6 into the envelope 10 is known in the prior art, e.g. see the U.S. patents cited above, which are incorporated by reference.

I claim:

1. A direct dispensing and self-contained surgical suture package comprising a first part having a strippable envelope, and self-contained therein a second part containing a suture and confined with:

a back panel whose perimeter comprises a first top edge, a right and left side edge, and a bottom edge;

a strand flap foldably connected to the bottom edge; and two opposite side flaps foldably connected to the right and left side edges respectively, the improvement comprising:

a label flap foldably connected to the entire first top edge, the label flap perimeter having a second top edge which is substantially parallel to and above the first top edge; and a chevron flap foldably connected to but distinct from the entire second top edge, the second part configured so that the strand flap is folded onto the back panel, the two opposite side flaps are folded onto said strand flap, the label flap is folded onto said side flaps, and the chevron flap is inserted between said side flaps and said strand flap.

2. A package of claim 1 having at least one retention slit contained in at least one of said side flaps.

* * * * *